United States Patent [19]
Catani et al.

[11] Patent Number: 5,998,177
[45] Date of Patent: Dec. 7, 1999

[54] PROCESS FOR PROCESSING SUCROSE INTO GLUCOSE

[75] Inventors: Steven J. Catani, Athens, Ga.; Stephen A. Roth, Gladwyne; Edward J. McGuire, Furlong, both of Pa.; Juan L. Navia, Athens, Ga.

[73] Assignee: Neose Technologies, Inc., Horsham, Pa.

[21] Appl. No.: 09/195,680

[22] Filed: Nov. 19, 1998

[51] Int. Cl.$^6$ ............................ C12P 19/04; C12P 19/02; C12N 9/10

[52] U.S. Cl. ............................ 435/101; 435/97; 435/105; 435/193

[58] Field of Search .................... 435/101, 105, 435/97; 438/193

[56] References Cited

U.S. PATENT DOCUMENTS

| | | |
|---|---|---|
| 4,133,875 | 1/1979 | Hilllman . |
| 4,150,116 | 4/1979 | Taubman et al. . |
| 4,169,825 | 10/1979 | Eigen et al. . |
| 4,263,052 | 4/1981 | Bichsel et al. . |
| 4,277,563 | 7/1981 | Kerkhoffs . |
| 4,299,677 | 11/1981 | Venkatasubramanian et al. . |
| 4,317,880 | 3/1982 | Heady . |
| 4,335,207 | 6/1982 | Heady . |
| 4,340,673 | 7/1982 | Stoudt et al. . |
| 4,356,262 | 10/1982 | Heady ...................................... 435/101 |
| 4,533,633 | 8/1985 | Weidenbach et al. ................... 435/176 |
| 4,637,835 | 1/1987 | Nagle . |
| 4,681,771 | 7/1987 | Adachi et al. . |
| 4,742,006 | 5/1988 | Bringer et al. . |
| 4,774,183 | 9/1988 | Fan . |
| 4,956,289 | 9/1990 | Wrasidlo et al. ........................ 435/176 |
| 5,002,759 | 3/1991 | Gaffar et al. . |
| 5,095,106 | 3/1992 | Gaffar et al. . |
| 5,169,679 | 12/1992 | Palanisamy . |
| 5,314,810 | 5/1994 | Kono et al. .............................. 435/101 |
| 5,478,732 | 12/1995 | Kunz et al. . |
| 5,524,075 | 6/1996 | Rousseau et al. . |
| 5,659,028 | 8/1997 | Coussement et al. . |

OTHER PUBLICATIONS

Computer Abstract 95(07):B0022 Hang et al., "Enzymatic conversion of sucrose to ketose by funal extracellular frutosyltansferase" Biotechnology Let (1995)17(3)295–298.

*Primary Examiner*—Herbert J. Lilling
*Attorney, Agent, or Firm*—Oblon, Spivak, McClelland, Maier & Neustadt, P.C.

[57] ABSTRACT

The present invention relates to a process of preparing commercial quantities of glucose from sucrose, a process of preparing commercial quantities of glucose and a branched fructan from sucrose, a reactor for practicing same.

12 Claims, 2 Drawing Sheets

PROCESS FOR PROCESSING SUCROSE INTO GLUCOSE

BACKGROUND OF THE INVENTION

1. Field of the Invention

The present invention relates to a process of preparing commercial quantities of glucose from sucrose, and a reactor for practicing same. In particular, the present invention relates to a process for preparing glucose from sucrose by contacting sucrose with a β-2,1-fructosyltransferase and a β-2,6-fructosyltransferase, followed by isolating glucose and a branched fructan, thereby enhancing production efficiencies.

2. Description of the Background

Glucose is a saccharide that is found throughout nature, either as a monosaccharide or incorporated into polysaccharides. Glucose is used clinically as a fluid and nutrient replenisher, as a carbon source in the culturing of microorganisms, and is widely used as a food additive.

Glucose has been prepared commercially from starch (Dean, Gottfried, *Advan. Carbohyd. Chem.* 5, 127 (1950) and by acid hydrolysis of sucrose. In spite of the availability of the starting materials for preparing glucose the cost of this material remains high, relative to the cost of the starting materials. Accordingly, commercial syntheses of glucose can be improved.

Fructans are found throughout nature (*Science and Technology of Fructans*, 1993 ed. M. Suzuki and N.J. Chatterton, CRC Press, Inc.). In plants, there are four fructans described 1) inulin, a 2,1- linked fructan found mainly in dicots, such as Jerusalem artichokes and chicory roots; 2) levan or phlein, a 2,6-linked fructan found in some monocots such as timothy; 3) a 2,1- and 2,6- branched fructan found in monocots such as barley, blue agave and wheat; and 4) a fructan of the neoseries, a 2,1-and 2,6-linked fructose on the glucose. The glucose is internal in these molecules, instead of terminal. Fructose residues are then linked 2,1-and 2,6-to both terminal fructose, creating a complex structure (asparagus). Many plants produce more than one of these fructans.

In yeast and fungi, 2,1-linked fructans have been reported.

In bacteria, two fructans have been described 1) an inulin 2,1-fructan from *Streptococcus mutans* and 2) a levan 2,6-linlked fructan has been described from *Bacillus subtilis, Zymomonas mobilis*, and many others.

Inulins are comprised of β-2,1-linked fructose chains, linked to an α D-glucoside; they have a linear structure and typically comprise many β-O-fruc tofuranose units. The average chain length and molecular weight distribution will depend on both the plant species, the growth phase, and the preparation method. Average chain lengths of 10 to 25 are common, in which case the individual units have about 9 to 24 fructose units.

Branched inulins have been reported, which comprise a linear chain of β-2,1-linked fructose chains, linked to an α D-glucoside, having branched thereon, β-2,6 fructose units. Such a branched inulin material has been reported having been isolated from the sap of the blue agave plant (G.O Aspinall and P.C. Das Gupta *Proceeding of the Chemical Society* 1959 718–722 and *M. N. Satyanarayana Indian J. of Biochem and Biophys.* (1976) 13:408–412) and from barley leaves (Simmen et al., *Plant Physiol.* (1993) 101:459–468).

The properties of an inulin may vary depending on the chain length and the degree of branching. Compositions comprising linear short chain inulins having a degree of polymerization of about 3 to 7 fructose units have been used as reduced calorie sugar substitutes (DE 4,003,140). Longer chain inulins have been uses is fat mimetics and branched fructans may be used as both.

Coussement et al. U.S. Pat. No. 5,659,028 discloses branched fructo-oligosaccharides consisting of a chain which comprises mainly fructose units and has a preferred chain length of 2 to 15 units, on which are fixed one or more side chains mainly composed of fructose units.

In the area of glucose production, Nagle et al. U.S. Pat. No. 4,637,835 report the preparation of glucose and other saccharides from an α-cellulose using a calciurm chloride catalyst and hydrogen ions.

Miyawaki et al. U.S. Pat. No. 5,524,075 report the production of high purity glucose by saccharifying liquefied starch with an enzyme.

Venkatasubramanian et al. U.S. Pat. No. 4,299,677 report the direct separation of fructose and glucose from a mixture of glucose and fructose by ion exKchange membranes.

Harada et al. U.S. Pat. No. 5,169,679 report the use of fructans composed mainly of β-2,1 bonds having a molecular weight of from 2,000 to 20,000,000 as food additives such as, for example, bulking agents or fat substitutes, for producing low calorie foods.

Kurz et al. U.S. Pat. No. 5,478,732 report a method for obtaining intermediate-chain inulins (e.g., a degree of polymerization of 10–12) by treatment of crude inulin suspensions with a hydrolase enzyme. During the enzymatic treatment, short-chain components are degraded to mono- and disaccharides while long-chain inulins are separated off, then converted to a dry form.

Adachi et al. report in U.S. Pat. No. 4,681,771 that when sucrose (G-F) is contacted with an enzyme having fructose transferring activity (hereinafter referred to as a fructosyltransferase), a low caloric, low-cariogenic sweetener composition is obtained which comprises glucose, sucrose, the trisaccharide ($GF_2$), the tetrasaccharide ($GF_3$) as well as minor amounts of fructose, pentasaccharide ($GF_4$) and hexasaccharide ($GF_5$). The amount of higher linear inulins drops off dramatically, the majority fraction being inulin $GF_{2-3}$.

Kono et al. U.S. Pat. No. 5,314,810 report that the half-life of an immobilized fructosyltransferase used in the reaction with sucrose can be improved by support on a granular carrier such as chitosan derivative or an anion exchange resin. Such a supported enzyme is reported to allow for the industrial production of a low cariogenic sweetener composition.

Heady U.S. Pat. No. 4,317,880 reports the production of novel fructose polymers and high fructose syrups from sucrose by the combined action of a fructosyltransferase enzyme and a glucose isomerase enzyme preparation.

A method of producing glucose and/or fructose irom sucrose is reported by Catani et al. in co-pending U.S. application Ser. No. 09/019,709 filed on Feb. 6, 1998.

Present methods for preparation of glucose from sucrose however, have suffered from poor efficiency, such that the production of commercial quantities of glucose can be improved.

In addition, there remains a need for processes for preparing commercial quantities of polysaccharides such as linear and branched inulins.

SUMMARY OF THE INVENTION

It is an object of the present invention to provide a process for preparing commercial quantities of glucose from sucrose.

It is another object to provide a process for preparing commercial quantities of the glucose and a branched fructan from sucrose.

The objects above may also be accomplished with a process for preparing glucose, by contacting sucrose with a β-2,1-fructosyltransferase and a β-2,6-fructosyltransferase in a reactor to produce reaction products comprising glucose and a branched fructan, followed by isolating glucose and a branched fructan.

In another embodiment, a process for preparing glucose may be achieved, by contacting sucrose sequentially first with a chain extending β-2,1-fructosyltransferase and second with a branching β-2,6-fructosyltransferase in a reactor to produce reaction products comprising glucose and a branched fructan, which is nearly depleted of sucrose.

The present invention is based, in-part, on the discovery that a combination of fructosyltransferases can be used to prepare glucose from sucrose (GF) with greater efficiency. In addition, branched fructans produced during the formation of glucose by the reaction of sucrose and two fructosyltransferases may be isolated in commercial quantities to further enhance the economic value of the present process.

BRIEF DESCRIPTION OF THE DRAWINGS

A more complete appreciation of the invention arid many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
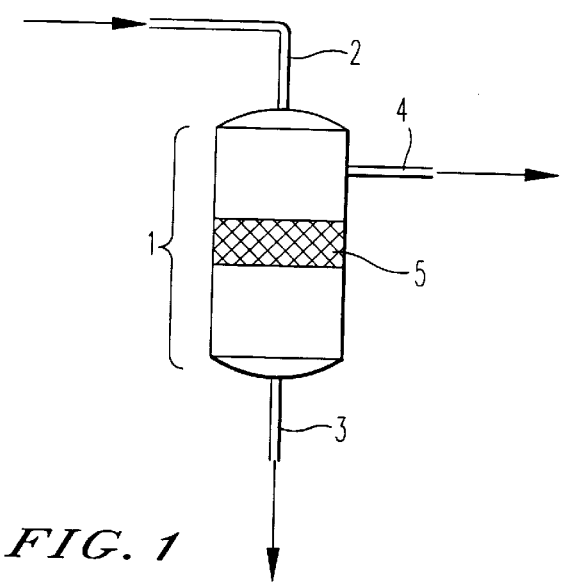
FIG. 1 depicts a flow diagram in which sucrose is converted to glucose and a branched fructan.

Glucose is a staple article of commerce and is sold for pharmaceutical and food uses. A branched inulin fructan has good performance in organoleptic tests and possesses bulking properties similar to sucrose for food use, as does non-branched inulins, but without inducing excessive gas upon consumption. A branched levan fructan also has good bulking properties for food use.

As used herein, the term "β-2,1-fructosyltransferase" refers to any enzyme or enzymes capable of transferring fructose moieties from sucrose as a donor, to sucrose or another saccharide (e.g., a fructan) as acceptors and forms β2,1 linkages. The fructose unit is preferably transferred in the furanose form. In addition, it is preferable that the β-2,1-fructosyltransferase is selective for fructose in the furanose form as an acceptor. In plants, these enzymatic activities are specifically provided for by a sucrose:sucrose 1-fructosyltransferase (1-SST) and fructan:fructan 1-fructosyltransferase (1FFT) (See Pollock et al. *Annu Rev. Plant Physiol. Plant Mol. Bio.* 42, 77–101 (1991). A β-2,1 fructosyltransferase isolated from S. mutans exhibits activity to transfer fructose to both sucrose and a fructan. The result of transferring the fructose moiety of sucrose is the production of a glucose unit. The β-2,1-fructosyltransferase may transfer fructose to the $C_1$ position of a terminal fructose (e.g forming linear chain extensions) or to the $C_1$ position of a linear fructan (e.g., a β2,6-linked levan) forming branching points. Some fructosyltransferases will have both activities (e.g., chain extension and branching), however, some fructosyltransferases will have only one activity. The selection of suitable chain extending and/or branching fructosyltransferases is within the level of skill to those of ordinary skill in the art.

Non-limiting examples of suitable β-2,1-fructosyltransferases may be obtained from microorganisms of the genus Aspergilus such as *A. oryzae* ATCC 20498; A. sp. ATCC 20524; *A. awamori, A. sydowi* and *A. niger* ATCC 20611; from the genus Penicillium, such as *P. jancezewskii* ATCC 10115 and 26546; *P. nigricans*, from the genus Fusarium, such as *F. lini* IAM 5011; and from the genus Aureobasidium, such as *A. pullulans* ACTT 9348; *Streptococcus mutans* ATCC 25175; and *A. pullulans var. melanigenum* A-8 ATCC 20612. Suitable enzymes may also be obtained from yeasts and other microorganisms such as the genus Saccharomyces, such as *S. cerevisiae*; the genus Rhodotorula, such as *R. lutinis*; the genus Pichia, such as *P. miso*; the genus Hansenula, such as *H. miso*; the genus Candida, such as *C. tropicali*; and from higher plants, such as asparagus, dahlia tubers, chicory roots, and the Jerusalem artichoke, as described in JP-A-56-154967 and JP-B-59-53834.

One particularly preferred enzyme is a bacterial β-2,1-fruetosyltransferase which may be obtained from a gene isolated from *Streptococcus mutans*. In particular S. mutans ATCC 25175 may be a source of a fructosyltransferase gene. The fructosyltransferase may be obtained as a fusion construct with a heterologous protein sequence. A suitable fusion protein is, for example, the fructosyltransferase isolated from *Streptococcus mutans* fused to the C-terminal of glutathione-S-transferase.

The coding sequence of the *Streptococcus mutans* fructosyltransferase, lacking the predicted signal sequence may be isolated from Streptococcus mutans strain ATCC 25175 by PCR which may be used to form a transformant which expresses a fructosyltransferase fusion protein. Another suitable fructosyltransferase gene sequence from *Streptococcus mutans* strain GS-5 is reported by Shiroza. T. and Kuramitsu, H. K. *J. Bacteriol.*, 170, 810–816 (1988).

As used herein, the term "β-2,6-fructosyltransferase" (also known as a levan synthetase) refers to any enzyme or enzymes capable of transferring fructose moieties from sucrose as a donor, to sucrose or another saccharide (e.g., a fructan) as an acceptor forming β2,6-linkages. The fructose unit is preferably transferred in the furanose form. In addition, it is preferable that the β-2,1-fructosyltransferase is selective for fructose in the furanose form as an acceptor. This specifically describes a sucrose:fructan 6-fructosyltransferase (6-SFT) (See Sprenger et al. *Proc. Natl Acad. Sci. USA*, 92, 11652–11656) (1995)) and a fructan:fructan 6G-fructosyltransferase (6G-FFT) (see. Vijn et al. The Plant Journal (1997) 11(3) 387–398). A result of transferring the fructose moiety of sucrose under the action of a β-2,6 fructosyltransferase is the production of a glucose unit. The β-2,6-fructosyltransferase may transfer fructose to the $C_6$ position of a terminal frictose (e.g forming linear chain extensions) or to the $C_6$ position of a linear fructan (e.g.,a β 2,1-linked inulin) forming branching points. Some fructosyltransferases will have both activities (e.g., chain extension and branching), however, some fructosyltransferases will have only one activity. The selection of suitable chain extending and/or branching fructosyltransferases is within the level of skill to those of ordinary skill in the art.

A suitable β-2,6-fructosyltransferase may be obtained from plant sources such as barley leaves and grasses. Such a β-2,6-fructosyltransferase is described from barley leaves by Simmen et al. *Plant Physiol.*(193) 101:459–468; Duchateau et al. *Plant Physiol.* (1995) 107:1249–1255. Levansucrase having a β-2,6-fructosyltransferase activity is also available from *Bacillus subtilis* (ATCC 6051) and *Zymomonas mobilis*. Purification, cloning and expression of a barley sucrose:frutan 6-fructosyltransferase is described by Sprenger at al. *Proc. Natl, Acad. Sci., USA* Vol. 92, pp. 11652–11656 (1995) and FEBS Lett 1997 Jan 6:400(3):355-8.

The present process provides for the reaction of sucrose with both a β-2,1-fructosyltransferase and β-2,6-fructosyltransferase, however, it is within the scope of the present invention to use additional glycosyltransferases, including other fructosyltransferases which do not interfere with the reaction of either a β-2,1-fructosyltransferase or a β-2,6-fructosyltransferase.

The following descriptions of fructosyltransferases applies independently to both the β-2,1-fructosyltransferase and β-2,6-fructosyltransferase.

The fructosyltransferases may be immobilized on a carrier having a primary to quaternary amine as described in U.S. Pat. No. 5,314,810.

In a preferred embodiment, the fructosyltransferases are at least partially purified. As used herein the term "purified" means that the enzyme has been purified, at least partially from the host organism from which it was produced naturally. Purification preferably results in at least partial removal of degradative enzymes such as inulinases which would degrade the fructan, and proteases which may degrade the fructosyltransferase enzyme. Preferably the enzyme is purified to a degree such that there is the absence of degradative enzymes. Widen the source of the enzyme is a transfected *E. coli* microorganism, a crude cell lysate may be used when the transfected *E. coli* has no native degradative enzymes.

In a preferred embodiment, each of the purified fructosyltransferases has a ratio of synthetic to degradation activity of $\geq 1,000$ to 1, more preferably $\geq 1,500$ to 1 and even more preferably $\geq 2,000$ to 1 (e.g., for every cleavage of a fructan linkage, there are preferably at least 1,000 linkages of fructose formed). Where one unit equals one Emole of monsaccharide transferred to an acceptor per minute, a crude *A. niger* growth supernatant contains ~90 units/mg protein, and a DEAE-purified *A. niger* preparation has ~2,000 units/mg protein. 10 μg of DEAE-purified preparation has sufficient activity to convert completely one liter of 50% sucrose to glucose and a linear fructan in about one day at 50° C. Alternatively, the same enzyme preparation may operate continuously, and with no drop in efficiency, for at least two weeks at 50° C., while sucrose is continually added.

Each of the fructosyltransferases may be purified, to an activity of from 90 to 3,000 U/mg, preferably from 100 to 2,000 U/mg. In a preferred embodiment, each of the fructosyltransferases will have an activity of $\geq 100$ U/mg, preferably $\geq 150$ U/mg, even more preferably $\geq 200$ U/mg.

A third fructosyltransferase is a 2,6-G-fructosyltransferase which transfers fructose to the $C_6$ hydroxyl group of glucose. Such a 2,6-G-fructos yltransferase preferably uses sucrose as a fructose donor. A suitable 2,6-G-fructosyltransferase may be isolated from natural sources by conventional methods known to those of ordinary skill in the art. Non-limiting examples of suitable sources include onions, asparagus and all Liliaceous plants.

When used in conjunction with a linear β-2,1 chain extending fructosyltransferase and a β-2,6-chain extending fructosyltransferase, star fructan may be formed which comprises linear β-2,1 and β-2,6-chains. Such a compound may be useful as a polyvalent support, as a bunking agent for food and as a cross-linking agent or core for polymers.

The starting material for the present process will be sucrose or a sucrose containing composition. Sucrose refers to the disaccharide in refined or raw form, as a solution or dry, from any sucrose raw material source, e.g., sugar cane, or sugar beets. Preferably the amount of sucrose contained in the sucrose raw material is $\geq 10$ wt. %, more preferably $\geq 20$ wt. %, even more preferably $\geq 50$ wt. %, most preferably $\geq 70$ wt. %. The feed stock may contain other materials so long as they do not significantly interfere with the conversion of sucrose to glucose (e.g 1-kestose (G1-2F1-2F).

Sucrose may be introduced in any of the forms as described above. In order to maintain the overall ionic strength and concentration of the reaction medium, however, sucrose is continuously or intermittently introduced in dry form or in solution. The rate and frequency of sucrose addition to the reaction mixture will be such as to maintain a high rate of production of oligosaccharide and will in part depend on the nature and specific activity of the fructosyltransferase, the reaction temperature and the rates of removal of glucose and fructan. The determination of the optimum rate and frequency of sucrose addition can be accomplished by routine experimentation and is within the level of skill of those of ordinary skill in the art.

The process of the present invention is preferably conducted in aqueous solution.

The concentration of sucrose in the reaction medium is not particularly limited and may be 50 mM up to saturation. In terms of weight percent, the amount of sucrose in the reaction solution may be 1 to 80% by weight, based on the total weight of the reaction mixture, typically from 40 to 80% w/w, preferably from 50 to 70 % w/w and more preferably about 60% w/w.

The branched fructan structure may vary depending on the reaction conditions selected. Within the context of the present invention, branched fructans comprising two basic linkages may be formed: 1) fructose:fructose linked β-2,1-; and 2) fructose:fructose linked β-2,6. Specific branched fructan structures provided for include 1) a linear β-2,1-inulin with β-2,6-branches; 2) a linear β-2,6-levan with β-2,1-branches; 3) a linear β-2,1-inulin with β-2,6-branches which contains β-2,1-branches; and 4, 6-linear β-2,6-levan with β-2,1-branches which contains β-2,6-branches. The addition of branch points to any linear chain which itself is a branching point may be continued. It will be appreciated by those of ordinary skill in the art that the fructan may comprise a glucose unit, a result of initial transfer of fructose to sucrose.

In one embodiment, a linear inulin fructan comprising β-2,1-linkages is formed under the action of a chain-extending β-2,1-fructosyltransferase, followed by branching with fructose units under the action of a branching β-2,6-fructosyltransferase. Sucrose would be the fructose donor for both fructosyltransferases. Sucrose and the terminal fructose of a fructan would be acceptors for the β-2,1-fructosyltransferase, while a linear fructan chain would be an acceptor for a β-2,6-fructosyltransferase. The linear inulin fructan comprising β-2,1-linkages may be formed in one or more stages, the use of a one stage process favoring the formation of a greater number of inulin chains of low DP, the use of a process comprising more than one stage favoring the production of fewer but longer inulin chains (e.g., higher DPs). In order to form longer inulin chains, fructan formation is induced with a portion of the sucrose to be converted, followed by addition of the remaining sucrose. Such a procedure for forming extended linear fructans (e.g higher DPs) is described by Catani et al. in co-pending U.S. Ser. No. 09/019,709, filed on Feb. 6, 1998, the entire contents of which are hereby incorporated by reference.

In another embodiment, a linear levan fructan comprising β-2,6-linkages is formed under the action of a β-2,6-fructosyltransferase, followed by branching with fructose units under the action of a β-2,1-fructosyltransferase. Sucrose would be the fructose donor for both fructosyltransferases. Sucrose and the terminal fructose of a fructan would be an acceptor for the β-2,6-fructosyltransferase while a linear fructan chain would be an acceptor for a β-2,1-fructosyltransferase. The linear levan fructan comprising β-2,6-linkages may be formed in one or more stages, the use of a one stage process favoring the formation of a greater number of levan chains of low DP, the use of a process comprising more than one stage favoring the production of fewer but longer levan chains (e.g., higher DPs). Ir order to form longer levan chains, fructan formation is induced with a portion of the sucrose to be converted, followed by addition of the remaining sucrose. Such a procedure for forming extended linear levan fructans is as described for the preparation of extended linear inulin fructans.

A linear levan fructan comprising β-2,6 linkages containing branching fructose units linked β-2,1-may be used as a bulking agent for food and food sweeteners. Such a fructan will typically have a linear levan fructan backbone comprising from 2 to 15 fructose units, preferably from 3 to 10, even more preferably from 4 to 7, which are β-2,6 linked to a glucose. Appended thereto will be one or more fructose units linked β-2,1-, forming branching points. The branching point may occur randomly on the linear levan fructan backbone. The molecular weight of such a fructan may range from about 700 to 3,600 gms/mol. Each branching point may itself be chain extended.

In another embodiment, the simultaneous action of both a β-2,1-fructosyltransferase and a β-2,6-fructosyltransferase on sucrose may give rise to a fructan comprising β2,1 and β-2,6 linkages, both branching and linear. Each fructosiiltransferise uses sucrose as the fructose donor and may use sucrose and/or a fructan as an acceptor. In addition, each fructosyltransferase may form either linear or branching linkages.

In another embodiment a linear inulin or linear levan fructan is branched under the action of both a β-2,1-fructosyltransferase and a β-2,6-fructosyltransferase. Each fructosyltransferase uses sucrose as the fructose donor and a fructim as an acceptor. In addition, each fructosyltransferase may form either linear or branching linkages.

Each of the fructans described above may be further elaborated to comprise one or more glucose units by the action of a glucosyltransferasc which uses a fructan as an acceptor and preferably uses sucrose as a glucose donor.

One advantage of forming branched fructans, is that the efficiency of formation of glucose is enhanced relative to the formation of only linear fructans since every branching group formed from sucrose will yield a unit of glucose. When a linear fructan is formed from sucrose, the first coupling of fructose to sucrose, a reaction which consumes two units of sucrose, will produce only one unit of glucose. As such, branched fructans synthesis from sucrose offers a highly efficient method of synthesizing glucose.

The reaction of sucrose with fructosyltransferases may be conducted over a wide temperature range. The reaction temperature may be room temperature, i.e. 18 to 25° C., up to temperatures just below the temperature where rapid inactivation of the fructosyltransferases occurs. A preferred temperature range is 25 to 60° C. More preferably, the reaction is conducted at a temperature of 35 to 55° C. Most preferably, the temperature is 30 to 50° C.

The aqueous reaction solutions may be unbuffered or bufftred at the appropriate pH using well-known buffer components, such as citrate, phosphate, and TRIS buffers. The use of a buffer is preferred when the reaction is conducted for an extended period of time, such as two weeks.

The reaction of sucrose with fructosyltransferases is conducted for a time sufficient to produce commercial quantities of glucose. The reaction time may be 2 to 48 days, depending on the size of the batch. When conducted in a continuous manner, a 10 mL volume may react at a rate of 2.5 g/hr, without a significant lose of activity, for a period of from 2 to 4 weeks.

The pH of the reaction of sucrose with fructosyltransferases is not particularly limited and the optimum pH of the reaction may vary depending on the specific enzyme used. Typically the pH will be from 4.0 to 8.0, preferably from 5.0 to 7.5, more preferably about 6.0.

The present process may be conducted in either a batchwise or continuous mode. The continuous reaction may be conducted by circulating a reaction mixture through an ultrafiltration apparatus whereby the product(s) are continually removed as the permeates from ultrafilters, a transferase enzyme being retained in the retentate from the ultrafilters. Fresh substrate and fresh enzyme may be added, as needed, to replace those that have become inactivated, addition to the reaction mixture being at the same rate in which the permeates arc removed from the ultrafilters.

The reaction of sucrose with a β-2,1-fructosyltransferase anad a β-2,6-fructosyltransferase may be conducted in a tubular reactor.

The tubular reactor will typically comprise a length of tubing, a pump for moving the reaction stream through the tube, an inlet for reactants and an outlet for reaction products.

The tubular reactor may be made of conventional reactor materials known to those of skill in the art. For example a tubular reactor may be made from stainless steel, glass lined stainless steel, or a polymer such as high density polyethylene, polypropylene, polyvinyl chloride or a polyester. In a preferred embodiment, the tubular reactor is made of polyvinyl chloride.

The tubular reactor will typically take the form of a pipe, the length and diameter of which may vary depending on the specific reaction being conducted. Generally a tube and have an inner diameter of from 1 to 24", preferably from 4 to 20", more preferably from 6 to 10".

A pump is provided to move the contents of the tubular reactor along the length of the reactor. Conventional pumps known to those of ordinary skill in the art may be used. Non-limiting examples of suitable pumps are:

Typically the pump will be provide sufficient force to provide a flow rate of 0.1 to 2 ft/sec, preferably from 0.2 to 1 ft/sec more preferably from 0.3 to 0.7 ft/sec. Preferably, the pump will produce a flow which behaves as a solid plug.

The inlet for the tubular reactor is not particularly limited and may comprise simply an opening which will allow introduction of reactants, either as an initial charge or continuously over the course of operation of the reactor. Reactants may being metered into the reactor, either gravimetrically or by a pump. The reactants may be introduced in solid form such as a powder, or as a solution in a suitable solvent.

The reactor may also be equipped with additional inlets, as described above, located along the length of the reactor, downstream of the initial inlet. These inlets may be used to add additional reactants at various point along the reaction stream.

The outlet for the product is not particularly limited and may take the form of a direct take off of the entire reactor contents from the reactor stream, or provide for selective removal of a reaction product. Selective removal of product may be by a size exclusion filter.

The length of the reactor will vary depending on the specific reaction and the reaction conditions such as the rate of flow through the reactor and the temperature.

The reactor may also be equipped with a temperature control system such as a heater or cooler. The ability to adjust the temperature will preferably vary throughout the length of the reactor, allowing for different temperature zones over the length of the reactor.

In one embodiment, sucrose is reacted with a β-2,1-fructosyltransferase in a first portion of a tubular reactor, followed by reaction with a β-2,6-fructosyltransferase in a downstream portion. Prior to reaction with the a β-2,6-fructosyltransferase, the β-2,1-fructosyltransferase may be deactivated by heating for a sufficient time and temperature, typically about 65 to 95° C., preferably from about 75 to 90° C., even more preferably about 85° C., for about one minute. Alternatively, a deactivation zone may comprise removal of the biocatalyst from the flow of the tube reactor, such as via a size exclusion membrane or the like. Deactivation may also be accomplished by introduction of a suicide substrate for the biocatalyst which deactivates the biocatalytic activity. Preferably, the fructosyltransferase is deactivated by thermal deactivation.

Levansucrase having a β-2,6-fructosyltransferase activity using a fructan as an acceptor, which is available by expression from a *Bacillus subtilis* (ATCC 6051), may be especially used, which provides for the efficient use of sucrose in the formation of β-2,6-linkages of fructose to the inulin chain. Such a fructosyltransferase may be obtained by conventional means known to those of ordinary skill in the art. When sucrose is efficiently reacted, a separation problem of glucose from residual sucrose is simplified.

In a preferred embodiment, the sucrose concentration after the action of a β-2,6-fructosyltransferase, if any, is ≦20 wt. %, more preferably ≦10 wt. %, even more preferably ≦5 wt. %, even more preferably ≦1 wt. %.

The reaction may also be conducted in a reactor or series of reactors, which may be equipped with suitable inlet reactants and outlets for products. The outlets may be selective for the removal of a specific product. Selectivity may be obtained by providing suitable separators which permit the removal of product and return of other materials to the reactor. A separator may be in the form of a membrane or a chromatography column. In some cases, a separator may comprise a plurality of membranes and/or chromatography columns providing for the selective removal of the desired product.

After the reaction to produce glucose, the fructosyltransferases may be inactivated by heating a reaction mixture to about 100° C. for from 10 to 15 minutes. If desired, the enzymes may be removed from the reaction mixture either before or after heat inactivation by means of ultrafiltration through a filter of suitable size.

Typically, the fructan will possess a linear backbone of fructose units in the β-O-fructofuranose, form β-2,1-linked. The number of β-O-fructofuranose units will typically be from 4 to 20, preferably from 4 to 15, more preferably from 4 to 8. Grafted on to the linear fructan backbone will be one or more β-O-fructofuranose units linked β-2,6-to the backbone. The number and density of fructose units grafted onto the backbone may vary, however typically, on average there will be at least 1 grafting fructose for every 5β-2,1-linearly linked fructose units, preferably at least 1 for every 4, more preferably at least 1 for every 3, even more preferably at least 1 for every 2. These ratios refer only to the number of branching points found on the linear backbone.

In another embodiment, the branched fructan may be chain-extended on branching fructose with β-O-fructofuranose units linked β-2,1-to the branching fructose unit, providing a branched fructan structure having a comb like structure. The number of β-O-fructofuranose units linked β-2,1-to the branching fructose may vary depending on the reaction conditions and will typically be from 2 to 20, more preferably from 2 to 10, even more preferably from 2 to 8 fructose units will be appended on to individual branching fructose units. It is not necessary for each branching fructose unit to bear the same number of chain extending fructose units. The term comb polymer is well known in the field of polymer chemistry, such that the structure of branched fructan described herein is clear to those of ordinary skill in the art.

It is also within the scope of the present invention to form branches and chain extended branches on individual comb chains which themselves are grafted onto a linear 2,1-linked fructan. The number and density of fructose units grafted onto the individual comb chains may vary, however, typically, on average there will be at least 1 grafting fructose for every 5β-2,1-linearly linked fructose units, preferably at least 1 for every 4, more preferably at least 1 for every 3, even more preferably at least 1 for every 2. These ratios refer only to the number of branching points found on the linear comb chain. The number of β-O-fructofuranose units linked β-2,1-to the branching fructose on the comb chain may vary depending on the reaction conditions and will typically be from 2 to 20, more preferably from 2 to 10, even more preferably from 2 to 8 fructose units will be appended on to individual branching frucotose units. It is not necessary for each branching fructose unit to bear the same number of chain extending fructose units.

For the purposes of illustration specific details are provided for the preparation of glucose from sucrose using at least a β-2,1-fructosyltransferase and a β-2,6-fructosyltransferase.

Sucrose and a β-2,1-fructosyltransferases are reacted in a reactor. The reactor may comprise an inlet for sucrose and an outlet for glucose. As the degree of polymerization increases, the concentration of glucose will also increase such that. it is possible that the rate of glucose-forming reaction will decrease. Accordingly in a preferred embodiment, glucose is removed from the reaction medium, during the reaction. The glucose may be removed by conventional methods known to those of ordinary skill in the art such as by membrane filtration or chromatography. Within the context of the present invention, chromatography includes ion exchange and gel exclusion techniques, known to those of ordinary skill in the art. A pump may be used to increase the pressure against the merlibrane or chromatography column. In a preferred embodiment, the outlet for gluccose comprises a membrane which permits the flow of glucose from the reaction medium, without allowing sucrose, fructan or fructosyltransferase to pass through.

A β-2,6-fructosyltransferase is then added, which upon reaction with sucrose, provides branching of the linear chain.

Glucose may be removed continuously, batchwise or semibatchwise, however, in a preferred embodiment, glucose is removed continuously from the reaction medium.

The glucose may be isolated and purified by conventional methods known to those of ordinary skill in the art such as by filtration which may also be followed by crystallization.

In a preferred embodiment, the fructan is also removed from the reaction mixture, more preferably, the fructan is removed continuously from the reaction mixture. A fructan may be removed by conventional methods known to those of ordinary skill in the art such as by membrane filtration or chromatography, such as ion exchange or gel exclusion. In a preferred embodiment, an outlet for fructan comprises a membrane which permits the flow of fructan from the reaction medium, without allowing sucrose, glucose or fructosyltransferase to pass through. Alternatively, the fructan may be separated from the reaction mixture, returning sucrose and glucose to the reaction mixture.

In a preferred embodiment the amount of fructan produced, based on the starting weight of sucrose is ≧10 wt. %, preferably ≧20 wt. %, even more preferably ≧30 wt. %, even more preferably ≧40 wt. %, and most preferably ≧50 wt. %.

In a preferred embodiment the yield of glucose produced, based on the reacted weight of sucrose, is from 25 to 50 wt. % preferably ≧25 wt. %, preferably ≧33 wt. %, even more preferably ≧37 wt. %, even more preferably ≧40 wt. %, and most preferably about 50 wt. %.

Within the context of the present invention, commercial quantities are defined as a rate of production of glucose of from $10^3$ to $10^5$ kg/day aLnd will preferably be an amount of ≧1,000 kg/day, preferably ≧2,000 kg/day, even more preferably ≧5,000 kg/day. In addition, the rate of production of commercial quantities is relative to the amount of sucrose starting material. Therefore the above identified rates of production are based on a unit processing of 6,000 kg of sucrose. Accordingly the term "commercial quantities" does not ricfcr to an absolute amount, but rather refers to a commercially acceptable rate of production.

In order to increase the efficiency of glucose production, in a preferred embodiment for batchwise chain elongation, each batch will comprise from 20 to 25 wt. % of the product of the previous reaction. Accordingly, after an initial batch of chain elongation is completed, from 75 to 80 wt. % of the reactants are removed, the remaining 20–25 wt. % remaining as a reactant for a second batch of chain elongation. Therefore the 20–25 wt. % of the first reaction product is charged to a reactor with sucrose and β-2,1-fructosyltransferase. In this fashion, the transfer of fructose from sucrose with the β-2,1-fructosyltransferase will be in the presence of a higher concentration of higher fructans, therefore favoring the formation of additional higher fructans, rather than trisaccharide (F-F-G). Since the production of higher fructans produces glucose more efficiently, this provides for an even more efficient method of forming glucose.

In a further preferred embodiment, the efficiency of the process may be increased further by recovering unreacted sucrose, if any, from the product of chain elongation (the β2,1-fructosyltransferase) or branching (the β-2,6-fructosyltransferase). Typically the action of a fructosyltransferase with sucrose will yield a reaction mixture comprising glucose, unreacted sucrose, fructan and fructose. Removal of unreacted sucrose and recycling back as a feedstock for a fructosyltransferase, greatly enhances the efficiency of glucose production.

For example sucrose may be removed by conventional chromatographic techniques known to those of ordinary skill in the art. As a specific example simulated moving bed techniques may be used to separate glucose, higher fructans ($DP_5$ and higher) and sucrose. The sucrose fraction will typically further comprise lower fructans $DP_3$ and $DP_4$ and glucose, all of which may be returned to a fructosyltransferase reaction, increasing the efficiency of glucose production.

Typically a simulated moving bed technique will use as a support, a salt of an anionic exchange resin, such as the sodium salt of a styrene-diviniyl benzene sulfonic acid resin which has a degree of crosslinking of from 4 to 6%. When the degree of crosslinking of the resin is above 6%, the efficiency of separation decreases. When the degree of crosslinking of the resin is below 4%, the mechanical integrity of the resin is undesirable. A suitable resin in available from Dow chemical as DOWEX® ion-exchange resin.

Separation of glucose may also be accomplished by size exclusion techniques using conventional hollow-type-membranes known to those of ordinary skill in the art. The sequential combination of the commercially available size exclusion membranes $G_{10}$ and $G_5$ provides for the effective isolation of glucose as well as a fraction comprising sucrose and lower fructans which may be recycled to the reactor.

Now referring to FIG. 1, where 1 depicts a reactor, 2 depicts an inlet for sucrose, 3 depicts a outlet for glucose, 4 depicts an outlet for a fructan and 5 depicts a separator which is permeable to glucose but not permeable to, sucrose, a fructosyltransferase or a fructan. Sucrose is introduced to the reactor via inlet 2 to a portion of reactor 1 which contains a β-2,1 fructosyltransferase and β-2,6 fructosyltransferase. In such a configuration, a partition is created such that fructans are concentrated on one side of the separator. The reactor is equipped with a glucose outlet 3, located on the glucose side of the separator 5. The outlet for fructan 4, may be equipped with a separator (not shown) which permits the passage of fructan, but does not permit passage of sucrose, glucose or fructos-yltransferases. If a membrane system is used to isolate fructan, typically the membrane will permit passage of glucose and sucrose, but not the branched fructan. Therefore, fructan has been effectively separated.

Figure 1A:
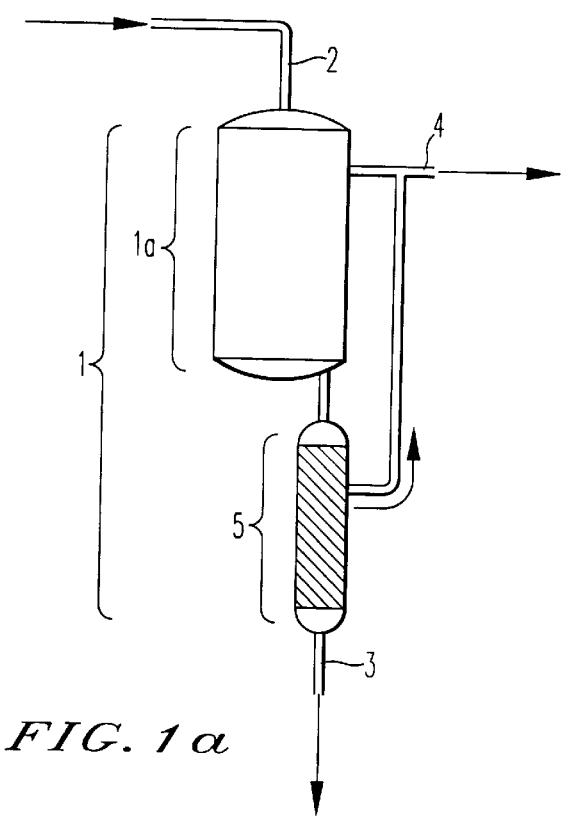
FIG. 1a depicts a flow diagram in which sucrose is converted to glucose and a branched fructan in a reactor vessel equipped with an external separator for glucose.

Now referring to FIG. 1*a*, where 1 depicts a reactor, 1*a* depicts a separate reactor portion, 2 depicts an inlet for sucrose, 3 depicts a outlet for glucose, 4 depicts an outlet for a fructan and 5 depicts a separator for glucose. Sucrose is introduced to the reactor via inlet 2 to a reactor portion 1*a* of reactor 1, which contains a β-2,1-fructosyltransferase and a β-2,6-fructosyltransferase. In such a configuration, glucose is separated from the reaction medium by separator 5, before being removed via glucose outlet 3. During the separation of glucose, the remaining materials may be recycled to reactor portion 1*a*. The outlet for fructan 4, may be equipped with a separator (not shown) which permits the passage of fructan, but does not permit passage of sucrose, glucose or fructosyltransferases.

In another embodiment, a reactor comprising an inlet for sucrose is equipped with an external separator, which separates both glucose and a fructan from sucrose. Unreacted sucrose, if any, may be returned to the reactor.

Figure 2:
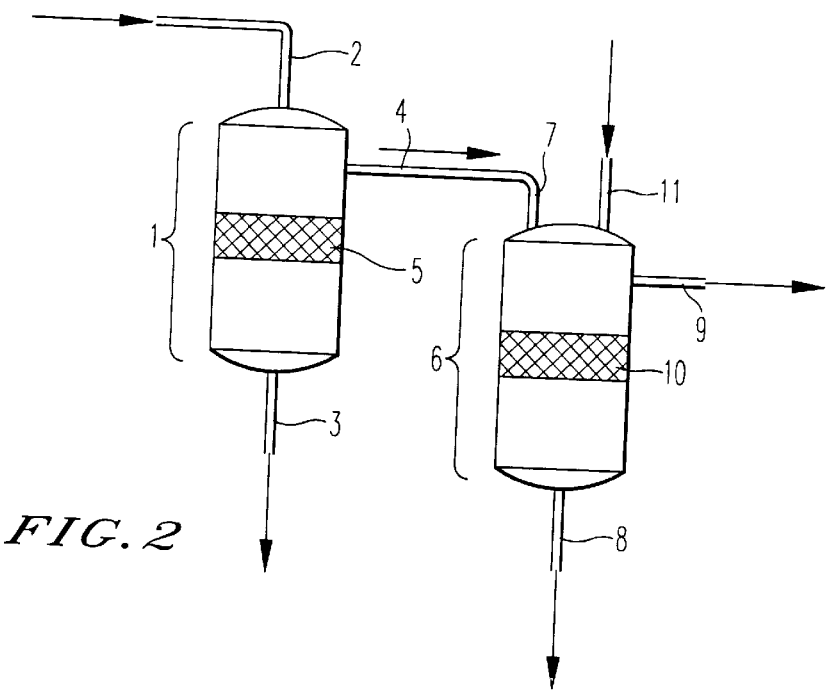
FIG. 2 depicts a flow diagram in which sucrose is converted to glucose and a branched fructan in two reaction vessels.

Now referring to FIG. 2, where 1 depicts a first reactor, 2 and 11 depict inlets for sucrose, 3 and 8 depict outlets for glucose, 4 depicts an outlet for a linear fructan, 5 and 10 depict separators which are permeable to glucose but not permeable to sucrose, a fructosyltransferase or a higher fructan, 6 depicts a second reactor, 7 depicts an inlet for a linear fructan and 9 depicts an outlet for a branched fructan. Two reactors are used, each partitioned with separators 5 and 10 which are permeable to glucose but impermeable to sucrose, fructosyltransferases or to linear or branched fructans. In the first reactor 1, the concentration of sucrose is such as to provide for the synthesis of linear β-2,1-inulin fructans, the product then being transferred to the second reactor 6 via inlet for a linear fructan. In a preferred embodiment, either the outlet for linear fructan 4 or the inlet for linear fructan 7 does not permit passage of an active fructosyltransferase. This may be accomplished by equipping either the outlet 4 or the inlet 7 with a membrane which does not permit the passage of a fructosyltransferase. Alternatively, either the outlet 4 or the inlet 7 may be equipped with a deactivation zone from fructosyltransferase, such as by heating for a sufficient time and temperature, typically about 65 to 95° C., preferably from about 70 to 90°, even more preferably about 85°, for about one minute. In the second reactor 6, a β-2,6-fructosyltransferase is contained in a portion of a second reactor 6 and a linear fructan is reacted with sucrose. Glucose is permitted to pass through separator 10 and is removed via glucose outlet 8. During the separation of glucose, the remaining materials may be recycled to reactor portion 6. The branched fructan may be removed via branched fructan outlet 9. The outlet for branched fructan 9, may be equipped with a separator (not shown) which permits the passage of branched fructans, but does not permit passage of sucrose, glucose or fructosyltransferases.

Figure 2A:
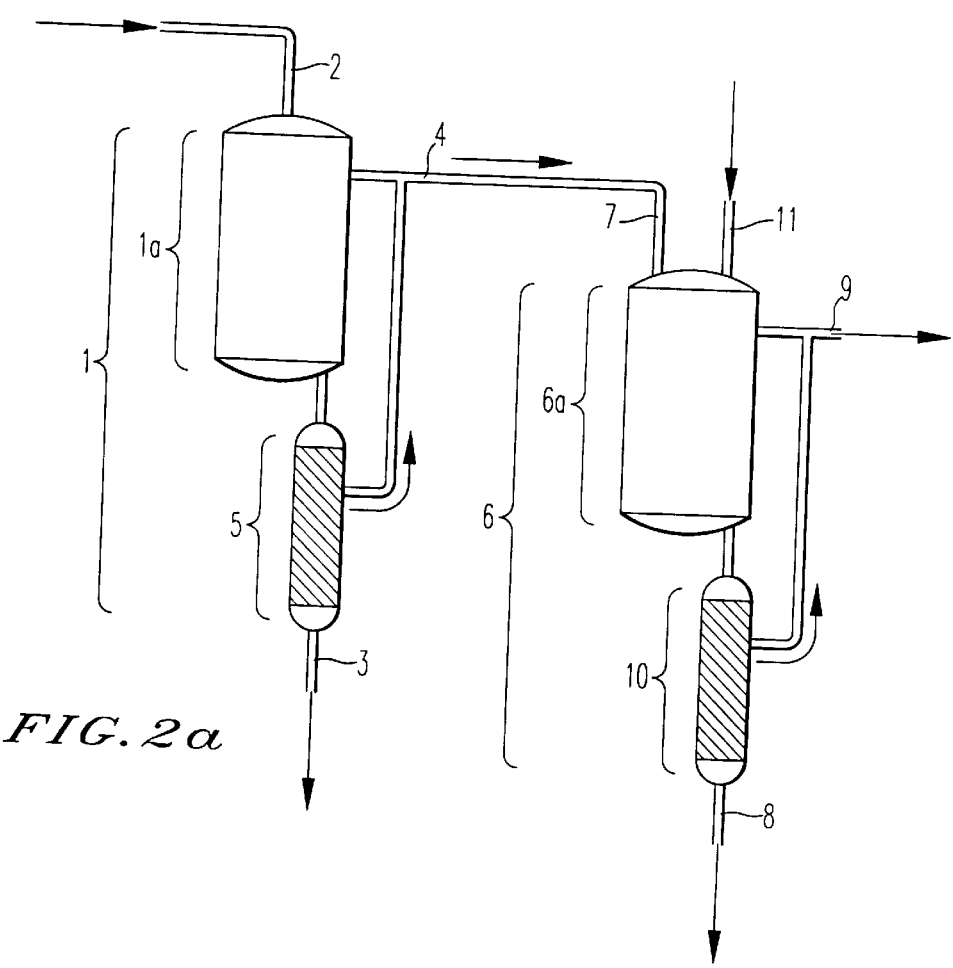
FIG. 2a depicts a flow diagram in which sucrose is converted to glucose and a branched fructan in two reaction vessels, each equipped with external separators for glucose.

Now referring to FIG. 2a, where 1 depicts a first reactor and 1a depicts a separate reactor portion, 2 and 11 depict inlets for sucrose, 3 and 8 depict outlets for glucose, 4 depicts an outlet for a linear fructan, 5 and 10 depict external separators which are permeable to glucose but not permeable to sucrose, fructosyltransferases or linear or branched fructan, 6 depicts a second reactor and 6a depicts a separate reactor portion, 7 depicts an inlet for a linear fructan and 9 depicts an outlet for a branched fructan. Two reactors are used, equipped with external separators 5 and 10 which are permeable to glucose but impermeable to sucrose, fructosyltransferases or to linear or branched fructans. In the first reactor portion 1a, the concentration of sucrose is such as to provide for the synthesis of linear fructans, β-2,1 linked, the product then being transferred to the second separate reactor portion 6a via inlet for a linear fructan 7. In a preferred embodiment, either the outlet for linear fructan 4 or the inlet for linear fructan 7 does not permit passage of an active fructosyltransferase. This may be accomplished by equipping either the outlet 4 or the inlet 7 with a membrane which does not permit the passage of a fructosyltransferase. Alternatively, either the outlet 4 or the inlet 7 may be equipped with a deactivation zone from fructosyltransferase, such as by heating for a sufficient time and temperature, typically about 65 to 95° C., preferably from about 70 to 90°, even more preferably about 85°, for about one minute. In the second reactor 6, a β-2,6-fructosyltransferase is contained in separate reactor portion 6a and a linear fructan is reacted with sucrose. Glucose is permitted to pass through separator 10 and is removed via glucose outlet 8. The branched fructan may be removed via branched fructan outlet 9. The outlet for branched fructan 9, may be equipped with a separator (not shown) which permits the passage of branched fructan, but does not permit passage of sucrose, glucose or β-2,6-fructosyltransferase. Both separators 5 and 10 are depicted with a recycle line to return materials other than glucose such as sucrose and lower fructan if necessary.

The process of the present invention is preferably conducted in a reactor suitable for making commercial quantities of branched fructan. Preferably the reactor comprises one or more inlets for introducing sucrose and/or the fructosyltransferase and a means for isolating commercial quantities of branched fructan from the reactor. The reactor may comprise multiple vessels, as illustrated in FIGS. 2 and 2a, functioning as a reactor system.

It is also within the scope of the present invention to conduct additional modifications of the enzymatically produced branched fructans by either conventional chemical modification or additional enzymatic modification. Non-limiting examples of chemical modification may include alkylation, esterification, dehydration, cyclization and partial hydrolysis. Non-limiting examples of enzymatic modification may include glycosylation.

A branched fructan of may be used as a bulking agent for foods and food sweeteners, which itself has sweetness.

Having generally described this invention, a further understanding can be obtained by reference to certain specific examples which are provided herein for purposes of illustration only and are not intended to be limiting unless otherwise specified.

Cloning and Expression Procedure:

The coding sequence of the Streptococcus mutan, fructosyltransferase, lacking the predicted signal sequence may be isolated from Streptococcus mutans strain ATCC 25175 by PCR. Two primers were designed and synthesized. The first, a 5'-TCTGCGGGATCCCAGGCAGATGAAG-CCAATTCAAC-3', contained a BamHI restriction site followed by sequence identical to the sequence immediately following the end of the predicted signal sequence in the Streptococcus mutans fruclosyltransferase coding sequence. The second, a 5'-TCTGCGAAGCTTTTATTTAAAACC-AATGCTTACACA-3', contained a HindIII restriction site followed by the reverse, complement sequence corresponding to the C-terminal end of the *Streptococcus mutans* fructosyltransferase coding sequence. Both primers were combined with genomic DNA isolated from *Streptococcus mutans* strain ATCC 25175 and used in the PCR. The resultant DNA fragment was digested with BamHI and HindIII and ligated to BamHI-HindIII digested plasmid, pGEX-KT-ext. This ligation resulted in the *Streptococcus mutans* fructosyltransferase coding sequence described above, being placed immediately downstream, in frame with the coding sequence of glutathione-S-transferase (GST). The pGEX-KT-ext-*Streptococcus mutans*-fructosyltransferase plasmid was transformed into E. coli BL21 cells. Protein expression from the resultant transformant resulted in intracellular accumulation of a GST-ext *Streptococcus mutans*-fructosyltransferase fusion protein.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing glucose from sucrose comprising:

i) contacting sucrose with a β-2,1-fructosyltransferase and β-2,6-fructosyltransferase to produce glucose; and ii) isolating glucose therefrom.

2. The process of claim 1, wherein said β-2,1-fructosyltransferase is obtained from an organism selected from the group consisting of *Aureobasidium pullulans, Aspergillus oryzae, Aspergillus awamori, Aspergillus sydowi,* Aureobasidium sp., *Aspergillus niger, Penicillium roquefortii, Streptococcus mutans, Penicillium jancezewskii* and higher plants.

3. The process of claim 1, wherein at least one of said β-2,1-fructosyltransferase or said β-2,6-fructosyltransferase is obtained by expression in a host of a fructosyltransferase gene which is not native to said host.

4. The process of claim 1, wherein said glucose is isolated continuously or semibatchwise.

5. The process of claim 1, wherein said reaction product further comprises a branched fructan and said process further comprises isolating said branched fructan.

6. The process of claim 5, wherein said branched fructan is continuously isolated.

7. The process of claim 1, wherein said glucose is isolated by membrane filtration or chromatography.

8. The process of claim 5, wherein said branched fructan is isolated by membrane filtration or chromatography.

9. The process of claim 1, wherein said β-2,1-fructosyltransferase is a chain extending fructosyltransferase.

10. The process of claim 1, wherein said β-2,6-fructosyltransferase is a branching fructosyltransferase.

11. The process of claim 1, wherein said β-2,1-tructosyltransferase is a branching fructosyltransferase.

12. The process of claim 1, wherein said β-2,6-fructosyltransferase is a chain extending fructosyltransferase.

* * * * *